US012626360B2

(12) United States Patent
Dhaouadi et al.

(10) Patent No.: US 12,626,360 B2
(45) Date of Patent: May 12, 2026

(54) AUTOMATED PROSTATE CANCER DETECTION AND DIAGNOSIS USING A BOOSTED ENSEMBLE OF BAGGING ENSEMBLE MODELS

(71) Applicant: Bot Image, Inc., Omaha, NE (US)

(72) Inventors: Jasser Dhaouadi, Omaha, NE (US); Ethan J. Ulrich, Omaha, NE (US); Randall W. Jones, Omaha, NE (US)

(73) Assignee: Bot Image, Inc., Omaha, NE (US)

( * ) Notice: Subject to any disclaimer, the term of this patent is extended or adjusted under 35 U.S.C. 154(b) by 478 days.

(21) Appl. No.: 18/114,174

(22) Filed: Feb. 24, 2023

(65) Prior Publication Data

US 2023/0267604 A1 Aug. 24, 2023

Related U.S. Application Data

(60) Provisional application No. 63/313,604, filed on Feb. 24, 2022.

(51) Int. Cl.
| | |
|---|---|
| *G06T 7/00* | (2017.01) |
| *A61B 5/00* | (2006.01) |
| *A61B 5/055* | (2006.01) |
| *G01R 33/56* | (2006.01) |
| *G01R 33/563* | (2006.01) |

(Continued)

(52) U.S. Cl.
CPC ............ *G06T 7/0012* (2013.01); *A61B 5/004* (2013.01); *A61B 5/055* (2013.01); *G01R 33/5602* (2013.01); *G01R 33/5608* (2013.01); *G01R 33/56341* (2013.01); *G06T 7/11* (2017.01); *G06T 7/33* (2017.01); *G16H 50/20* (2018.01); *G06T 2207/10088* (2013.01); *G06T 2207/30081* (2013.01)

(58) Field of Classification Search
None
See application file for complete search history.

(56) References Cited

U.S. PATENT DOCUMENTS

| | | |
|---|---|---|
| 2016/0292855 A1 | 10/2016 | Metzger et al. |
| 2019/0287023 A1 | 9/2019 | Kasahara et al. |

(Continued)

OTHER PUBLICATIONS

International Search Report and Written Opinion received in PCT/US2023/063282, mailed on Jun. 16, 2023 (8 pages).

*Primary Examiner* — Lennin R Rodriguezgonzalez
(74) *Attorney, Agent, or Firm* — Torrey Pines Law Group PC

(57) ABSTRACT

A computer system that analyzes medical-imaging data to assess a risk for prostate cancer is described. The computer system may compute features (including intensity, texture and/or spatial features) based at least in part on the medical-imaging data. Then, using a pretrained predictive model, the computer system may determine cancer predictions on a voxel-by-voxel basis, based at least in part on the computed features. Note that the pretrained predictive model may include a boosted parallel random forests (BPRF) model with a boosted ensemble of bagging ensemble models, where a given bagging ensemble model includes an ensemble of random forests models. Next, the computer system may provide feedback based on the cancer predictions for the voxels. For a given voxel, the feedback may include a cancer prediction and a location. In some embodiments, for the given voxel, the feedback may include an aggressiveness of the predicted cancer and/or a recommended therapy.

20 Claims, 13 Drawing Sheets

┌─ 200

RECEIVE MEDICAL-IMAGING DATA
210

COMPUTE FEATURES
212

DETERMINE CANCER PREDICTIONS
214

PROVIDE FEEDBACK
216

PERFORM ONE OR MORE ADDITIONAL OPERATIONS
218

(51) Int. Cl.
　　*G06T 7/11*　　　　(2017.01)
　　*G06T 7/33*　　　　(2017.01)
　　*G16H 50/20*　　　(2018.01)

(56) References Cited

U.S. PATENT DOCUMENTS

| | | |
|---|---|---|
| 2019/0370965 A1 | 12/2019 | Lay et al. |
| 2020/0278408 A1 | 9/2020 | Sung et al. |
| 2020/0370124 A1 | 11/2020 | Hall et al. |
| 2021/0097682 A1 | 4/2021 | Madabhushi et al. |

RETRIEVE
STUDY

PACS          COMPUTER
SYSTEM
100

CHECK FOR
NEW STUDIES

NEW
STUDY → SERIES
CHECK → SLICES
CHECK → VOLUMES
CHECK → QUALITY
ASSURANCE
RESULT

MISSING
SERIES

MISSING
SLICES

MODEL
ARCHITECTURE
1010

$$Pred(BPRF) = \sum_{i=1}^{n} w_i \left(\frac{1}{5} \sum_{j=1}^{5} Pred(RF_{i,j})\right)$$

Patient ID: #
Study:

Prostate Volume: 57.31 cc
Prostate Dimensions: 5.0 x 4.3 x 4.8 cm

ROI #1 : Index = 99.0

Zone: Central Gland

Estimated Size: 3.64 cc
Dimensions: 2.4 x 2.2 x 1.5 cm

AUTOMATED PROSTATE CANCER DETECTION AND DIAGNOSIS USING A BOOSTED ENSEMBLE OF BAGGING ENSEMBLE MODELS

CROSS-REFERENCE TO RELATED APPLICATIONS

This application claims the benefit of U.S. Provisional Application No. 63/313,604, filed Feb. 24, 2022, the entirety of which is incorporated herein by reference.

FIELD

The described embodiments relate to processing of medical images. Notably, the described embodiments relate to a processing of medical images to detect and/or diagnose a type of cancer (such as prostate cancer) using a pretrained predictive model that includes a boosted ensemble of bagging ensemble models.

BACKGROUND

Prostate cancer is the second most-common type of cancer among men. If detected and diagnosed early in the disease progression, prostate cancer can typically be treated successfully.

Screening tests are often performed in an attempt to find early-stage prostate cancer in individuals before they have symptoms. For example, prostate-specific antigen (PSA) blood tests are used to look for changes in the PSA level, because the probability of having prostate cancer increases with the PSA level. However, there is no set cutoff point that indicates whether or not a man has prostate cancer. Consequently, it remains unclear whether the benefits of prostate cancer screening outweigh the risks for most men.

When prostate cancer is suspected, e.g., based on the results of a screening test or patient systems, additional tests are usually used to detect and diagnose prostate cancer. For example, a urologist may perform a prostate biopsy on a patient. However, a prostate biopsy is an invasive procedure in which a thin, hollow needle is repeatedly inserted into the prostate to remove small cylindrical cores of prostate tissue for assessment by a pathologist.

Alternatively or additionally, medical imaging tests are often used to detected and diagnose prostate cancer. For example, different types of magnetic-resonance-imaging (MRI) scans or studies (such as diffusion weighted imaging or DWI, dynamic contrast enhanced or DCE MRI, and/or MR spectroscopy or MRS) are routinely used to acquire images of the prostate. In principle, MRI studies can be analyzed to: determine parameters of prostate tissue, identify abnormal areas, diagnose prostate cancer, and/or assess the extent (or stage) of the cancer.

In practice, accurate interpretation of medical images (such as MRI images) and prediction of prostate cancer remain challenging. This is the case whether the interpretations and predictions are performed solely by physicians (such as radiologists), jointly by physicians and computers (computer-aided diagnosis), or in an automated manner (solely by computer). For example, when medical images are interpreted by radiologists, there is often high inter-reader variability and a high false positive rate. Consequently, the limitations of existing analysis techniques adversely impact analysis performance and increase the costs of treating suspected or actual prostate cancer, which in turn increase the morbidity and mortality associated with this disease.

SUMMARY

A computer system that provides feedback is described. This computer system includes: an interface circuit; a computation device (such as a processor, a graphics processing unit or GPU, etc.) that executes program instructions; and memory that stores the program instructions. During operation, the computer system receives medical-imaging data associated with a pelvic region of an individual. Then, the computer system computes features associated with voxels corresponding to a prostate of the individual based at least in part on the medical-imaging data, where, for a given voxel, the features include: intensity features, texture features, and a spatial feature corresponding to a distance from a peripheral zone of the prostate to a transition zone of the prostate. Moreover, the computer system determines, on a voxel-by-voxel basis, cancer predictions for the voxels based at least in part on the computed features and a pretrained predictive model. This pretrained predictive model includes a boosted parallel random forests (BPRF) model, and the pretrained BPRF model includes a boosted ensemble of bagging ensemble models (such as classifiers), where a given bagging ensemble model includes an ensemble of random forests models. Next, the computer system provides the feedback based at least in part on the cancer predictions for the voxels, where, for the given voxel, the feedback includes: a cancer prediction and a location.

Note that the medical-imaging data may include MRI studies of the individual. For example, the MRI studies may include: transverse relaxation time-weighted (T2 W) images, apparent diffusion coefficient (ADC) images, and/or diffusion-weighted imaging (DWI) images.

Moreover, the computer system may segment the medical-imaging data to identify the voxels corresponding to the prostate. In some embodiments, the segmenting may identify sub-regions of the prostate.

Furthermore, the computer system may register a first volume corresponding to the ADC images and a second volume corresponding to the DWI images with a third volume corresponding to the T2 W images. The registration may include aligning the first volume and the second volume with the third volume, and correcting the second volume for distortion. Note that the registration may be based at least in part on mutual information between a give pair of volumes in the first volume, the second volume and the third volume. In some embodiments, the registration may be based at least in part on a Bayesian technique.

Additionally, the intensity features may include radiomics features and the texture features may include Haralick texture features (which may be a subset of the radiomics features).

In some embodiments, the boosted ensemble is based at least in part on an adaptive boosting technique and the bagging ensemble is based at least in part on a Bayesian estimator technique.

Moreover, the boosted ensemble may be computed sequentially and the bagging ensemble may be computed in parallel.

Furthermore, the feedback may include an image indicating first regions of the prostate where the cancer predictions exceed a first threshold value. In some embodiments, the feedback may include the image indicating second regions of the prostate where the cancer predictions are less than the first threshold value and greater than a second threshold value.

Additionally, the feedback may include an image with an at least partially transparent three-dimensional (3D) rendering of the prostate and one or more color-coded regions in the 3D rendering corresponding to cancer predictions exceeding a threshold value.

In some embodiments, for the given voxel, the feedback indicates an aggressiveness of predicted cancer based at least in part on the cancer predictions.

Note that the feedback may include or correspond to a recommended therapy based at least in part on the cancer predictions.

Another embodiment provides a computer for use, e.g., in the computer system.

Another embodiment provides a computer-readable storage medium for use with the computer or the computer system. When executed by the computer or the computer system, this computer-readable storage medium causes the computer or the computer system to perform at least some of the aforementioned operations.

Another embodiment provides a method, which may be performed by the computer or the computer system. This method includes at least some of the aforementioned operations.

This Summary is provided for purposes of illustrating some exemplary embodiments, so as to provide a basic understanding of some aspects of the subject matter described herein. Accordingly, it will be appreciated that the above-described features are examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
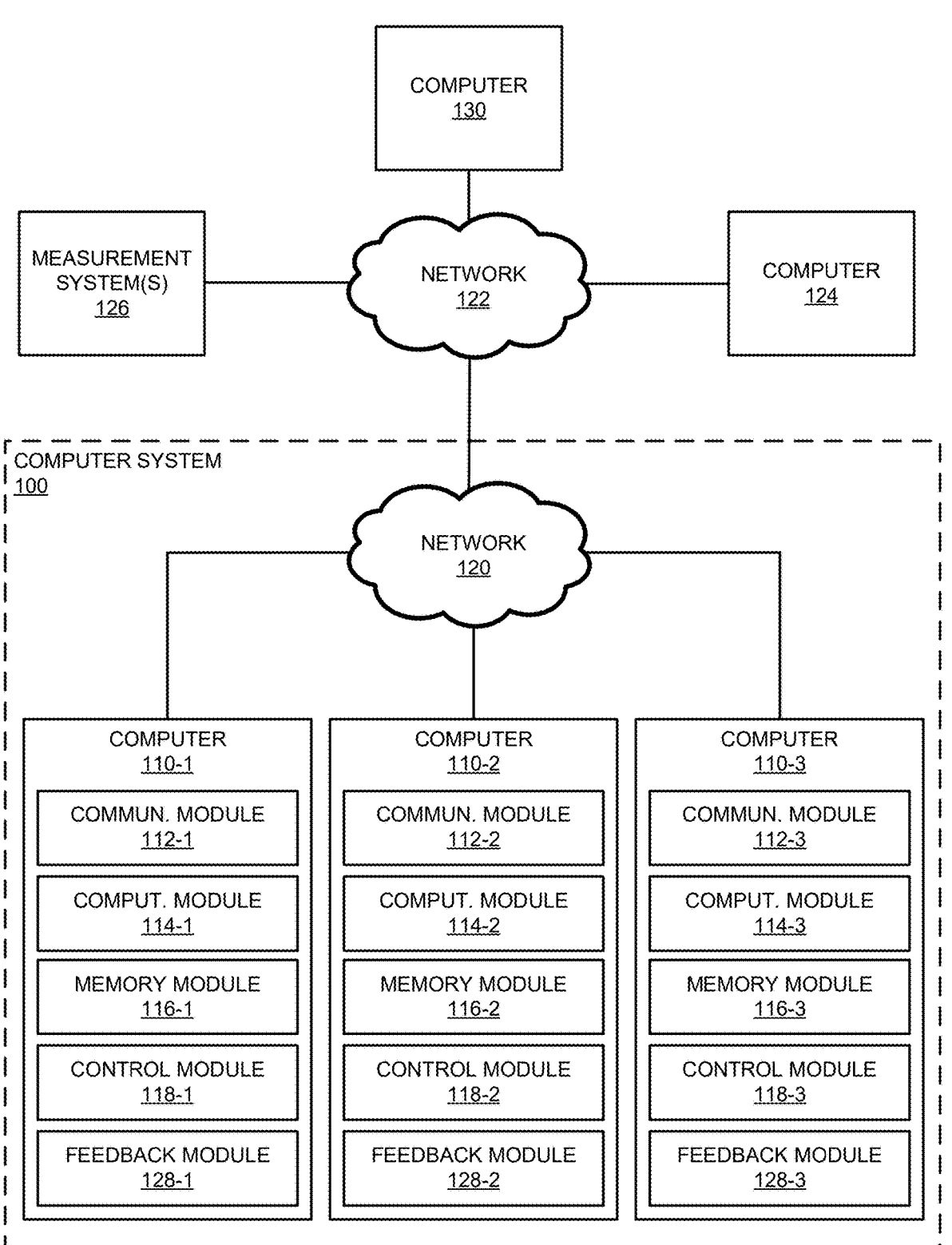
FIG. 1 is a block diagram illustrating an example of a computer system in accordance with an embodiment of the present disclosure.

A computer system that analyzes medical-imaging data (e.g., MRI studies) to assess a risk for prostate cancer is described. The computer system may compute features (including intensity features, texture features and a spatial feature) based at least in part on the medical-imaging data. Then, using a pretrained predictive model, the computer system may determine cancer predictions on a voxel-by-voxel basis, based at least in part on the computed features. Note that the pretrained predictive model may include a BPRF model with a boosted ensemble of bagging ensemble models (such as classifiers), where a given bagging ensemble model includes an ensemble of random forests models. Next, the computer system may provide feedback based on the cancer predictions for the voxels. For a given voxel, the feedback may include a cancer prediction and a location. In some embodiments, for the given voxel, the feedback may include an aggressiveness of the predicted cancer, information associated with disease progression (such as a disease stage) and/or a recommended therapy (e.g., based at least in part on the aggressiveness and/or the disease stage).

By providing the feedback, these analysis techniques may address the problems associated with existing prostate-cancer analysis techniques. Notably, the analysis techniques may provide quantitative insight into anomalous regions in the prostate. These capabilities may reduce or eliminate unnecessary biopsies of non-cancerous tissue and/or may provide more accurate or early detection of prostate cancer. Consequently, the analysis techniques may improve the accuracy and relevance of the feedback, which may provide improved detection, diagnosis, tracking of disease progression and treatment. Moreover, the feedback may enable further understanding of prostate cancer (and, more generally, a variety of types of cancer) and its progression, and may facilitate the development of new treatments.

In the discussion that follows, the analysis techniques are used to analyze MRI data, such as T2 W images, ADC images, and/or DWI images. However, the analysis techniques may be used to analyze a wide variety of types of MR images (which may or may not involve MRI, e.g., free-induction-decay measurements), such as: MRS with one or more types of nuclei, MR spectral imaging (MRSI), MR elastography (MRE), MR thermometry (MRT), magnetic-field relaxometry and/or another MR technique (e.g., functional MRI, metabolic imaging, molecular imaging, blood-flow imaging, diffusion-tensor imaging, etc.). More generally, the analysis techniques may be used to analyze measurement results from a wide variety of invasive and non-invasive imaging techniques, such as: X-ray measurements (such as X-ray imaging, X-ray diffraction or computed tomography at one or more wavelengths between 0.01 and 10 nm), neutron measurements (neutron diffraction), electron measurements (such as electron microscopy or electron spin resonance), optical measurements (such as optical imaging or optical spectroscopy that determines a complex index of refraction at one or more visible wavelengths between 300 and 800 nm or ultraviolet wavelengths between 10 and 400 nm), infrared measurements (such as infrared imaging or infrared spectroscopy that determines a complex index of refraction at one or more wavelengths between 700 nm and 1 mm), ultrasound measurements (such as ultrasound imaging in an ultrasound band of wavelengths between 0.2 and 1.9 mm), proton measurements (such as proton scattering), positron emission spectroscopy, positron emission tomography (PET), impedance measurements (such as electrical impedance at DC and/or an AC frequency) and/or susceptibility measurements (such as magnetic susceptibility at DC and/or an AC frequency).

We now describe embodiments of the analysis techniques. FIG. 1 presents a block diagram illustrating an example of a computer system 100. This computer system may include one or more computers 110. These computers may include: communication modules 112, computation modules 114, memory modules 116, and optional control modules 118. Note that a given module or engine may be implemented in hardware and/or in software.

Communication modules 112 may communicate frames or packets with data or information (such as measurement results or control instructions) between computers 110 via a network 120 (such as the Internet and/or an intranet). For example, this communication may use a wired communication protocol, such as an Institute of Electrical and Electronics Engineers (IEEE) 802.3 standard (which is sometimes referred to as 'Ethernet') and/or another type of wired interface. Alternatively or additionally, communication modules 112 may communicate the data or the information using a wireless communication protocol, such as: an IEEE 802.11 standard (which is sometimes referred to as 'Wi-Fi', from the Wi-Fi Alliance of Austin, Texas), Bluetooth (from the Bluetooth Special Interest Group of Kirkland, Washington), a third generation or 3G communication protocol, a fourth generation or 4G communication protocol, e.g., Long Term Evolution or LTE (from the 3rd Generation Partnership Project of Sophia Antipolis, Valbonne, France), LTE Advanced (LTE-A), a fifth generation or 5G communication protocol, other present or future developed advanced cellular communication protocol, or another type of wireless interface. For example, an IEEE 802.11 standard may include one or more of: IEEE 802.11a, IEEE 802.11b, IEEE 802.11g, IEEE 802.11-2007, IEEE 802.11n, IEEE 802.11-2012, IEEE 802.11-2016, IEEE 802.11ac, IEEE 802.11ax, IEEE 802.11ba, IEEE 802.11be, or other present or future developed IEEE 802.11 technologies.

In the described embodiments, processing a packet or a frame in a given one of computers 110 (such as computer 110-1) may include: receiving the signals with a packet or the frame; decoding/extracting the packet or the frame from the received signals to acquire the packet or the frame; and processing the packet or the frame to determine information contained in the payload of the packet or the frame. Note that the communication in FIG. 1 may be characterized by a variety of performance metrics, such as: a data rate for successful communication (which is sometimes referred to as 'throughput'), an error rate (such as a retry or resend rate), a mean squared error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a communication channel or link), and/or a ratio of an actual data rate to an estimated data rate (which is sometimes referred to as 'utilization'). Note that wireless communication between components in FIG. 1 uses one or more bands of frequencies, such as: 900 MHz, 2.4 GHz, 5 GHz, 6 GHz, 60 GHz, the Citizens Broadband Radio Spectrum or CBRS (e.g., a frequency band near 3.5 GHz), and/or a band of frequencies used by LTE or another cellular-telephone communication protocol or a data communication protocol. In some embodiments, the communication between the components may use multi-user transmission (such as orthogonal frequency division multiple access or OFDMA).

Moreover, computation modules 114 may perform calculations using: one or more microprocessors, ASICs, micro-controllers, programmable-logic devices, GPUs and/or one or more digital signal processors (DSPs). Note that a given computation component is sometimes referred to as a 'computation device'.

Furthermore, memory modules 116 may access stored data or information in memory that local in computer system 100 and/or that is remotely located from computer system 100. Notably, in some embodiments, one or more of memory modules 116 may access stored measurement results in the local memory, such as MRI data for one or more individuals (which, for multiple individuals, may include cases and controls or disease and healthy populations). Alternatively or additionally, in other embodiments, one or more memory modules 116 may access, via one or more of communication modules 112, stored measurement results in the remote memory in computer 124, e.g., via network 120 and network 122. Note that network 122 may include: the Internet and/or an intranet. In some embodiments, the measurement results are received from one or more measurement systems 126 (such as MRI scanners) via network 120 and network 122 and one or more of communication modules 112. Thus, in some embodiments at least some of the measurement results may have been received previously and may be stored in memory, while in other embodiments at least some of the measurement results may be received in real-time from the one or more measurement systems 126.

While FIG. 1 illustrates computer system 100 at a particular location, in other embodiments at least a portion of computer system 100 is implemented at more than one location. Thus, in some embodiments, computer system 100 is implemented in a centralized manner, while in other embodiments at least a portion of computer system 100 is implemented in a distributed manner. For example, in some embodiments, the one or more measurement systems 126 may include local hardware and/or software that performs at least some of the operations in the analysis techniques. This remote processing may reduce the amount of data that is communicated via network 120 and network 122. In addition, the remote processing may anonymize the measurement results that are communicated to and analyzed by computer system 100. This capability may help ensure computer system 100 is compatible and compliant with regulations, such as the Health Insurance Portability and Accountability Act, e.g., by removing or obfuscating protected health information in the measurement results.

Although we describe the computation environment shown in FIG. 1 as an example, in alternative embodiments, different numbers or types of components may be present in computer system 100. For example, some embodiments may include more or fewer components, a different component, and/or components may be combined into a single component, and/or a single component may be divided into two or more components.

As discussed previously, it is often challenging to accurately detect and diagnose prostate cancer (and, more generally, other types of cancer) using existing analysis techniques. Moreover, as described further below with reference to FIGS. 2-16, in order to address these challenges computer system 100 may perform the analysis techniques. Notably, during the analysis techniques, one or more of optional control modules 118 may divide the analysis among computers 110. Then, a given computer (such as computer 110-1) may perform at least a designated portion of the analysis. In particular, computation module 114-1 may receive (e.g., access) information (e.g., using memory module 116-1) specifying medical-imaging data that specify the prostate for one or more individuals. Note that the medical-imaging data may include or may correspond to MRI data. Then, computation module 114-1 may perform operations in multiple stages in an analysis pipeline. For example, as described further below with reference to FIG. 4-16, the analysis pipeline may include: automatic detection of inputs (such as MRI data), input quality testing (such as a series check, a slices check and/or a volume check), segmentation (such as identifying voxels corresponding to the prostate and/or sub-regions of the prostate), registration (such as aligning volumes associated with different types of MRI images and correcting for distortion), feature calculation (including intensity features, texture features and one or more spatial features) and/or cancer classification (such as a risk assessment or cancer predictions, e.g., aggressiveness of a predicted cancer, disease progression or a disease stage, etc., which may be computed using a pretrained predictive model).

In general, the pretrained predictive model may include a machine-learning model or a neural network, which may include or combine one or more convolutional layers, one or more residual layers and one or more dense or fully connected layers, and where a given node in a given layer in the given neural network may include an activation function, such as: a rectified linear activation function or ReLU, a leaky ReLU, an exponential linear unit or ELU activation function, a parametric ReLU, a tanh activation function, and/or a sigmoid activation function. As described further below with reference to FIG. 10, in some embodiments the pretrained predictive model may include a pretrained BPRF model, and the pretrained BPRF model may include a boosted ensemble of bagging ensemble models (such as classifiers), where a given bagging ensemble model includes an ensemble of random forests models. Moreover, the boosted ensemble may be based at least in part on an adaptive boosting technique and the bagging ensemble may be based at least in part on a Bayesian estimator technique. In some embodiments, the boosted ensemble may be computed in sequentially and the bagging ensemble may be computed in parallel. Additionally, as described further below with reference to FIGS. 11-12, the pretrained predictive model may have an improved receiver operator characteristic (ROC) and an improved free-response receiver operator characteristic (FROC) relative to other models or model architectures.

After performing at least some of the operations in the stages in the analysis pipeline, computation module 114-1 may output or provide information specifying the cancer classification. Then, the one or more of optional control modules 118 may instruct one or more of feedback modules 128 (such as feedback module 128-1) to generate a report about the one or more individuals (such a computer-aided diagnosis report with feedback, such as the cancer classification, a recommended therapy, etc.). As shown in FIGS. 13-16, the computer-aided diagnosis report may include one or more images illustrating the prostate and a suspected solid tumor location. Moreover, the one or more images may include a 3D rendering of the prostate and the suspected solid tumor location. Note that the one or more images may include color-coded regions corresponding to cancer predictions.

Furthermore, the one or more of optional control modules 118 may instruct one or more of communication modules 114 (such as communication module 114-1) to return, via network 120 and 122, outputs (such as the computer-aided diagnosis report, a Digital Imaging and Communications in Medicine or DICOM output, another digital imaging format for output transmission, etc.) to computer 130 associated with a physician of the one or more individuals.

Additionally, the one or more of optional control modules 118 may instruct one or more memory modules 116 (such as memory module 116-1) to optionally perform study deletion (such as deleting protected health information associated with the one or more individuals, such as the MRI data).

In these ways, computer system 100 may automatically and accurately analyze medical-imaging data associated with the one or more individuals. These capabilities may allow computer system 100 to detect and diagnose a type of cancer (such as prostate cancer) in an automated manner. Moreover, the information determined by computer system 100 (such as the treatment recommendation, e.g., whether or not to perform a subsequent prostate biopsy, radiation and/or a particular type of chemotherapy) may facilitate or enable improved use of existing treatments (such as precision medicine by selecting a correct medical intervention to treat a type of cancer, e.g., as a companion diagnostic for a prescription drug or a dose of a prescription drug) and/or improved new treatments. While the preceding discission illustrated the use of the analysis techniques for prostate cancer, more generally the analysis techniques may be used in conjunction with a wide variety of types of cancer, including different types of solid tumors (such as sarcomas, carcinomas or lymphomas) in organs such as: the bladder, the breast, the cervix, the colon, the rectum, the endometrium, the kidney, lips (and, more generally, oral cancer), the liver, the lungs (such as small cell lung cancer), the skin (such as melanoma or nonmelanoma skin cancer), the mesothelial lining (such as mesothelioma), the ovaries, the pancreas, fat and muscle tissue (such as sarcoma), the thyroid, the prostate, the brain (and, more generally, the central nervous system), lymph nodes, bone, etc. Consequently, the analysis techniques may facilitate accurate, value-added use of the measurement results, such as medical-imaging data.

Figure 2:
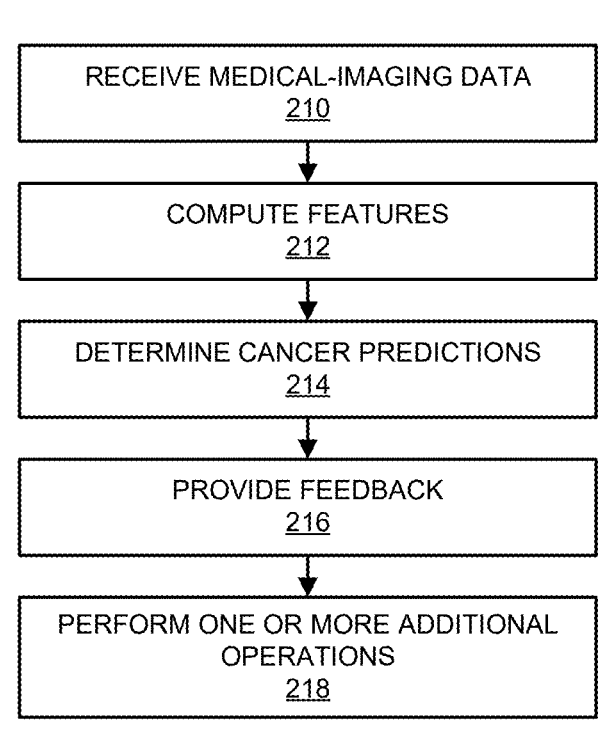
FIG. 2 is a flow diagram illustrating an example of a method for providing feedback using a computer system in FIG. 1 in accordance with an embodiment of the present disclosure.

We now describe embodiments of the method. FIG. 2 presents a flow diagram illustrating an example of a method 200 for providing feedback, which may be performed by a computer system (such as computer system 100 in FIG. 1). During operation, the computer system may receive medical-imaging data (operation 210) associated with a pelvic region of an individual. For example, the medical-imaging data may include MRI studies of the individual. In some embodiments, the MRI studies may include: T2 W images, ADC images, and DWI images. Note that ADC images may eliminate the T2 weighting otherwise inherent to DWI images, DWI images may be based on measurements of random Brownian motion of water molecules within a voxel of tissue, and T2 W may be a weighting used in MRI based on the length of time it takes for an MR signal to decay in the transverse plane. In some embodiments, a given MRI image may be acquired with a static external magnetic-field strength of 1.5 or 3.0 T, and the image (voxel) resolution may be, e.g., 1 $mm_3$ or 2 $mm^2$.

Then, the computer system may compute features (operation 212) associated with voxels corresponding to a prostate of the individual based at least in part on the medical-imaging data, where, for a given voxel, the features include: intensity features, texture features, and/or a spatial feature corresponding to a distance from a peripheral zone of the prostate to a transition zone of the prostate. Note that the intensity features may include radiomics features and the texture features may include Haralick texture features (which may be a subset of the radiomics features). For example, the Haralick texture features may include correlation $$\frac{\sum_{i=1}^{N}\sum_{j=1}^{N}p(i,j)ij - \mu_x\mu_y}{\sigma_x(i)\sigma_y(j)},$$

contrast $$\sum_{i=1}^{N}\sum_{j=1}^{N}(i-j)^2 p(i,j),$$

and/or entropy $$\sum_{i=1}^{N}\sum_{j=1}^{N}p(i,j)\log(p(i,j)),$$

where I and j represent discrete intensity values, p(i,j) represents an element in a normalized co-occurrence matrix (computed by P(i,j)/ΣP(i,j)), P(i,j) represents a gray-level co-occurrence matrix (GLCM), N represents a number of discrete intensity values in a neighborhood of pixels, $\mu_x$ represents a mean intensity $$\sum_{i=1}^{N}p_x(i)i, \; p_x(i) = \sum_{j=1}^{N}P(i,j)$$

represents marginal row probabilities, $\mu_y$ represents a mean intensity $$\sum_{j=1}^{N}p_y(i)j, \; p_y(j) = \sum_{i=1}^{N}P(i,j)$$

represents marginal column probabilities, and $\sigma_x(i)$ and $\sigma_y(j)$ represent standard deviations of $p_x(i)$ and $p_y(j)$, respectively.

In some embodiments, there may be 64 radiomics features associated with each pixel or voxel associated with the prostate, including: 4 intensity features and 13 texture features (such as smooth versus grainy), and the spatial feature may include a Euclidean distance to the central gland of the prostate (such as a distance to a border of the transition zone). Additionally, for the DWI series, the image channel associated with the highest b-value may be used for feature extraction.

Moreover, the computer system may determine, on a voxel-by-voxel basis, cancer predictions (operation 214) or classifications for the voxels based at least in part on the computed features and a pretrained predictive model. The pretrained predictive model may include a BPRF model, and the pretrained BPRF model may include a boosted ensemble of bagging ensemble models (such as classifiers), where a given bagging ensemble model includes an ensemble of random forests models. For example, the boosted ensemble may be based at least in part on an adaptive boosting technique and the bagging ensemble may be based at least in part on a Bayesian estimator technique. In some embodiments, the boosted ensemble may be computed sequentially and the bagging ensemble may be computed in parallel.

Next, the computer system may provide the feedback (operation 216) based at least in part on the cancer predictions for the voxels, where, for the given voxel, the feedback includes: a cancer prediction and a location (which may be used to guide treatment, e.g., to provide a treatment recommendation). Moreover, the feedback may include an image indicating first regions of the prostate where the cancer predictions exceed a first threshold value. Furthermore, the image may indicate second regions of the prostate where the cancer predictions are less than the first threshold value and greater than a second threshold value. Additionally, the feedback may include an image with an at least partially transparent 3D rendering of the prostate and one or more color-coded regions in the 3D rendering corresponding to cancer predictions exceeding a threshold value. Note that, for the given voxel, the feedback may indicate an aggressiveness of predicted cancer based at least in part on the cancer predictions. In some embodiments, the feedback may include or correspond to a recommended therapy based at least in part on the cancer predictions.

In some embodiments, the computer system may optionally perform one or more additional operations (operation 218). For example, the computer system may register a first volume corresponding to the ADC images and a second volume corresponding to the DWI images with a third volume corresponding to the T2 W images, where the registration may include aligning the first volume and the second volume with the third volume, and may include correcting the second volume for distortion. Moreover, the registration may be based at least in part on mutual information between a given pair of volumes in the first volume, the second volume and the third volume. Furthermore, the registration may be based at least in part on a Bayesian technique.

Alternatively or additionally, the computer system may segment the medical-imaging data to identify the voxels corresponding to the prostate. Note that the segmenting may identify sub-regions of the prostate.

In some embodiments of method 200, there may be additional or fewer operations. Furthermore, the order of the operations may be changed, and/or two or more operations may be combined into a single operation.

Figure 3:
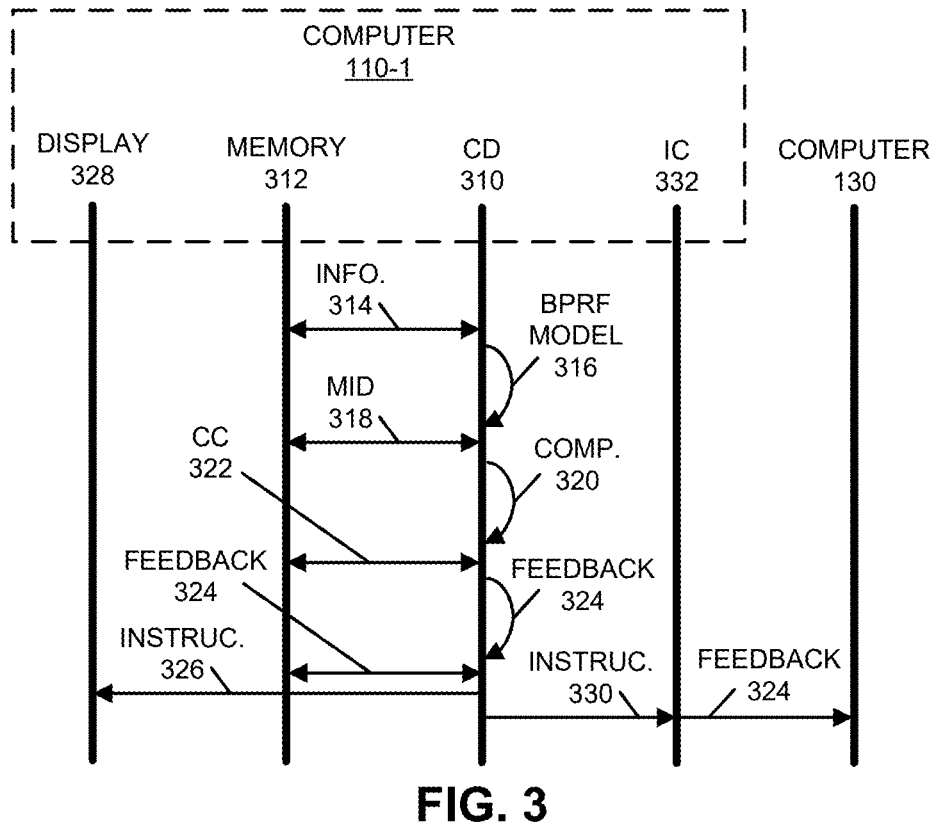
FIG. 3 is a drawing illustrating an example of communication between components in a computer system in FIG. 1 in accordance with an embodiment of the present disclosure.

Embodiments of the analysis techniques are further illustrated in FIG. 3, which presents a drawing illustrating an example of communication among components in computer system 100. In FIG. 3, a computation device (CD) 310 (such as a processor or a GPU) in computer 110-1 may access, in memory 312 in computer 110-1, information 314 specifying configuration instructions and hyperparameters for one or more predetermined or pretrained models, such as pretrained BPRF model 316 and/or one or more neural networks. After receiving the configuration instructions and the hyperparameters, computation device 310 may implement the pretrained BPRF model 316.

Moreover, computation device 310 may access in memory 312 information specifying medical-imaging data (MID) 318 that specify the prostate (and, more generally, at least a portion of the body) for at least an individual. After receiving medical-imaging data 318, computation device 310 may compute 320, using the pretrained BPRF model 316 and based at least in part on the medical-imaging data 318, cancer classification (CC) 322 for at least the individual. After or while performing the computations, computation device 310 may store results, including the cancer classification 322, in memory 312.

Next, computation device 310 may determine feedback 324 associated with at least the individual based at least in part on the cancer classification 322. This feedback may include a computer-aided diagnosis report, which may include one or more images. The feedback 324 may be stored in memory 312. Alternatively or additionally, computation device 310 may provide instructions 326 to a display 328 in computer 110-1 to display feedback 324. In some embodiments, computation device 310 may provide instructions 330 to an interface circuit 332 in computer 110-1 to provide feedback 324 to another computer or electronic device, such as computer 130.

While FIG. 3 illustrates communication between components using unidirectional or bidirectional communication with lines having single arrows or double arrows, in general the communication in a given operation in this figure may involve unidirectional or bidirectional communication.

We now further describe embodiments of the analysis techniques. The analysis techniques (which are sometimes referred to as 'ProststID™') may provide computer-aided diagnosis (CADx) and detection (CADe) for prostate cancer by post-processing MRI images of the prostate. The analysis techniques may be performed by a computer system (which may be locally or remotely located, e.g., a cloud-based computer system) that operates independently from a user's computer system, such as an MRI scanner or a Picture Archiving and Communication Storage (PACS) computer system. However, in other embodiments, the analysis techniques may be implemented or integrated with a user's computer system.

During operation, a user may provide MRI studies (e.g., in DICOM format) via a pre-established connection that securely connects the user's computer system to a computer system that performs the analysis techniques (such as computer system 100 in FIG. 1). For example, there may be an encrypted connection between the computer system a set of authenticated peers, such as the user's computer system.

The computer system may automatically detect new studies pushed to its local PACS and may trigger its analysis pipeline to start processing. Moreover, the computer system may perform multiple sequential filters and/or may interact actively (e.g., via email) with the users to ensure that the quality of input data meets its quality standards. The computer system may continue processing the studies by implementing computer-vision and graphics techniques (such as a pretrained neural network) in order to generate a color map reflecting or highlighting the prostate cancer predictions determined by a pretrained predictive model in the computer system (which is sometimes referred to as an 'artificial intelligence or AI inference module). Furthermore, the computer system may generate a report containing detailed information about any suspicious region(s) with a high likelihood to be cancerous. The computer system may convert the color map or overlay and the report to DICOM format and may provide them to the user via the secure connection. Additionally, the computer system may optionally delete all information associated with any completed study.

The analysis techniques may provide an AI solution that interprets medical images and that provides accurate predictions of prostate cancer. For example, the analysis techniques may reduce or eliminate the visual limitations of physicians, thereby improving their performance. Because the analysis techniques may improve the analysis performance and, thus, may improve the confidence of physicians that use the analysis techniques. Moreover, the analysis techniques may provide non-invasive and fast cancer prediction. For example, the average processing time may be 10 min., and the processing time may be further reduced by using parallel processing. Furthermore, the analysis techniques may lower the cost of cancer detection and diagnosis, and thus may reduce the cost of prostate cancer treatment.

In the present discussion, a DICOM instance may include a file in DICOM format, which often contain health information and a 2-dimensional (2D) image. Moreover, a DICOM series may include a set of DICOM files that contain one or more DICOM instances, which may be identified by a unique series identifier. Furthermore, a DICOM study may include a set of DICOM files that contain one or more DICOM series, which may be identified by a unique study identifier. Additionally, a field of view (FOV) may include the physical space dimensions that are defined, e.g., by an MRI technician during imaging acquisition.

Figure 4:
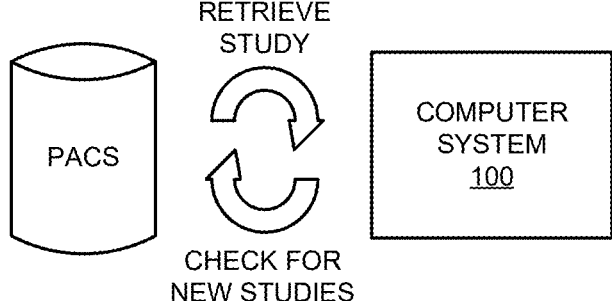
FIG. 4 is a drawing illustrating an example of automated detection of inputs to an analysis pipeline in accordance with an embodiment of the present disclosure.

In some embodiments, the analysis techniques may be implemented using an analysis pipeline. The analysis pipeline may include automatic detection of inputs. This is shown in FIG. 4, which presents a drawing illustrating an example of automated detection of inputs to an analysis pipeline, such as new DICOM studies. For example, the computer system may automatically detect new studies that have been sent to a user's PACS computer system. Once a new study is considered stable, the computer system may retrieve DICOM instances related to the new study from the user's PACS computer system.

Figure 5:
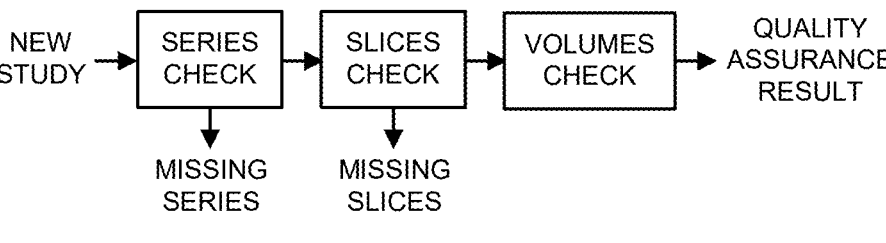
FIG. 5 is a drawing illustrating an example of input quality testing in an analysis pipeline in accordance with an embodiment of the present disclosure.

Then, the computer system may inspect each DICOM series of a new study for deficiencies. This is shown in FIG. 5, which presents a drawing illustrating an example of input quality testing in an analysis pipeline. Notably, the computer system may check if any of the series (such as the ADC series, the T2 W series and/or the DWI series) are missing. Moreover, the computer system may check if there are any geometric issues, such as missing DICOM instances (slices) in any of the DICOM series. Furthermore, the computer system may convert each DICOM series to an image volume, and the computer system may check if the volumes meet the minimum quality requirements (such as an image resolution of at least 0.625 mm in the XY plane, a thickness of a slice in the Z direction of 4.5 mm, an axial FOV of 20 cm$^2$ or 256×512, etc.). Table 1 summarizes MRI acquisition parameters for T2 W slices and DWI slices for a variety of MR scanners. The user may be notified, e.g., via email, if an error is detected during quality testing.

TABLE 1

| T2W Parameter | Values |
| --- | --- |
| Repetition time (ms) | 2975-9999 |
| Echo time (ms) | 96-125 |
| Flip angle (degrees) | 90-160 |
| Slice thickness (mm) | 3.0-4.0 |
| Square matrix size (pixels) | 320-512 |
| In-plane FOV (mm) | 140-200 |
| In-plane resolution (mm) | 0.273-0.573 |

| DWI Parameter | Values |
| --- | --- |
| Repetition time (ms) | 3360-6804 |
| Echo time (ms) | 52-85 |
| High b-value (s/mm$^2$) | 1400-2000 |
| Slice thickness (mm) | 3.0-4.0 |
| Square matrix size (pixels) | 118-256 |
| In-plane FOV (mm) | 140-256 |
| In-plane resolution (mm) | 0.547-1.695 |

Figure 6:
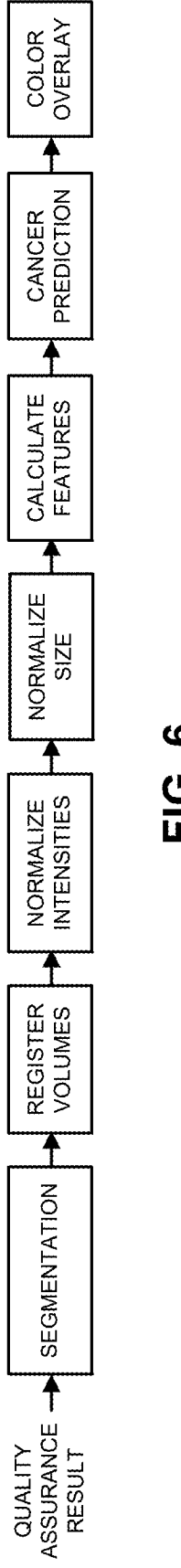
FIG. 6 is a drawing illustrating an example of computer-aided detection and diagnosis in an analysis pipeline in accordance with an embodiment of the present disclosure.

If all the series of the study pass quality filters, the image volumes for the T2 W, DWI and ADC may be passed to the computer-aided detection and diagnosis operation in the analysis pipeline. This is shown in FIG. 6, which presents a drawing illustrating an example of computer-aided detection and diagnosis in an analysis pipeline. Notably, during the computer-aided detection and diagnosis, the computer system may segment the volume corresponding to the prostate organ, producing a prostate mask volume. Then, the computer system may segment the volume corresponding to the sub-region of the prostate called the central gland, producing a central gland mask volume. For example, the segmenting may be performed using two 3D convolutional neural networks. Notably, a first 3D convolutional neural network may detect the prostate at low resolution in a T2 W series, and a second 3D convolutional neural network may then perform segmentation of a border of the prostate with higher accuracy (such as a variation on a deep residual network or ResNET). This segmentation of the border may identify a peripheral zone of the prostate and a transition (central) zone of the prostate.

Moreover, the computer system may register the DWI volume and the ADC volume to the T2 W volume using a rigid transformation based at least in part on anatomical reference points. The registration operation may use mutual information for the cost metric for aligning images of different modalities (such as ADC, DWI and T2 W). For example, the parameters of the rigid transformation may be determined using a Bayesian optimization technique that maximizes the mutual information cost function. In some embodiments, the Bayesian optimization technique uses the T2 W volume as a reference, and optimizes a shift and a rotation (or a best transformation) to align with the ADC volume. Then, the DWI volume may be aligned with the ADC volume. This latter operation may include correcting for distortion in the DWI volume relative to the T2 W volume, so that there is good rotation correspondence.

Next, the computer system may normalize image volume intensities to a predefined range (e.g., a minimum and a maximum intensity). Furthermore, the computer system may resize image volumes (e.g., normalized T2 W, normalized DWI, normalized ADC, prostate mask, and central gland mask) to a predefined size. For example, the centroid of the prostate may be calculated and used to define a 140 mm FOV region (edge-to-edge) centered on the prostate organ. Note that the volumes may be resampled to this FOV to a voxel grid of 512×512 in the XY plane. The voxel spacing in the Z dimension may be determined by the T2 W volume.

Additionally, the computer system may calculate image features using the image volumes (e.g., normalized T2 W, normalized DWI, normalized ADC, prostate mask, and central gland mask) using radiomics techniques, such as an intensity of a voxel or a function applied to the neighborhood of voxels surrounding a central voxel. Note that the image features may be calculated from individual image voxels (e.g., voxel intensity) and/or groups of voxels surrounding a reference voxel (e.g., mean voxel intensity, correlation, contrast, entropy, and/or another characteristic of the groups of voxels). Note that the calculated features may be stored as an image-feature data frame and/or the data frame may store the voxel index and image feature values for voxels corresponding to the prostate.

In some embodiments, the computer system may detect an anatomy of the prostate in the T2 W MRI image of the pelvis region. As noted previously, the detection may be accomplished using a 3D convolutional neural network that is trained to segment the prostate in T2 W image volumes. Moreover, the computer system may perform the detection using the features in the image-feature data frame as input to a pretrained predictive model, such as a classifier model that was trained on patient data with proven cancerous/benign diagnoses. This model may operate in a 2D slice-by-slice approach and may provide or produce a prediction for the likelihood of prostate cancer (or level of suspicion) for every voxel described in the image-feature data frame on a continuous scale. For example, the likelihood prediction may be a value between '0' and '1' for each voxel, with a value of 0 corresponding to a low likelihood of prostate cancer and a value of 1 corresponding to a high likelihood of cancer.

The computer system may use the predictions for the voxels in the image-feature data frame to create a probability map volume. Then, the computer system may convert the probability map volume to a color map volume (e.g., using an RGB colorization technique, which is described further below with reference to Tables 3 and 4), which may be overlaid on the T2 W volume using alpha blending to indicate the probability of cancer in the identified regions.

Figure 7:
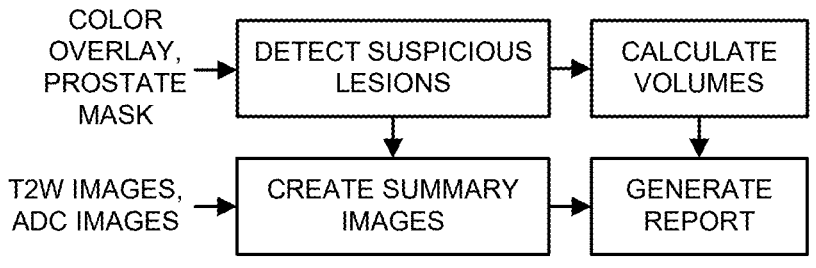
FIG. 7 is a drawing illustrating an example of computer-aided report generation in an analysis pipeline in accordance with an embodiment of the present disclosure.

Moreover, the computer system may take the image volumes and may generate a report that summarizes the results of the computer-aided detection and diagnosis. This is shown in FIG. 7, which presents a drawing illustrating an example of computer-aided report generation in an analysis pipeline. Notably, the computer system may calculate the approximate volume and dimensions of the prostate organ using the input prostate mask volume. Then, the computer system may detect regions of interest (ROIs) corresponding to regions with a high likelihood of cancer using the color overlay volume. Furthermore, the computer system may calculate the estimated volume and dimensions of a given ROI and may display or include them in the report. Next, the computer system may display or include them in the report the estimated sub-region (such as a peripheral zone or central gland) where an ROI occurs. For a given ROI, the computer system may use the ROI centroid to define 2D slice images for the T2 W series, the ADC series, and the color overlay. In some embodiments, these three slice images may be displayed or included in one row of the report. Additionally, for the given ROI, the computer system may produce and display or include a 3D rendering of the prostate organ with the 3D rendering of the ROI in the report. If no ROIs are detected, then the computer system may indicate in the report that there were no ROIs. Note that the report may include slices of the color overlay corresponding to the mid-gland, apex, and base levels of the prostate.

Figure 8:
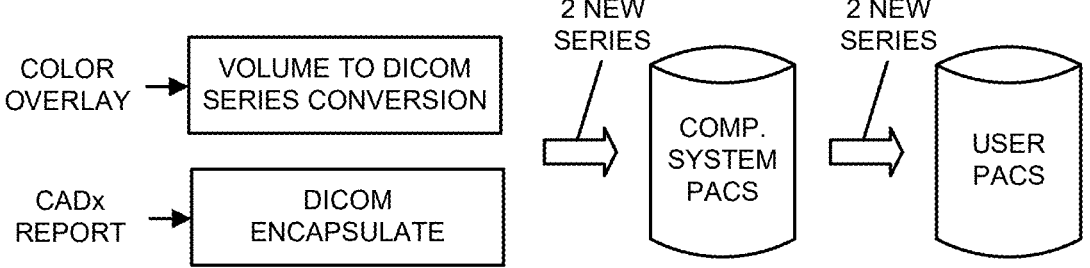
FIG. 8 is a drawing illustrating an example of providing outputs in an analysis pipeline in accordance with an embodiment of the present disclosure.

After completing these operations, the computer system may provide analysis results to a user. This is shown in FIG. 8, which presents a drawing illustrating an example of providing outputs (such as DICOM outputs) in an analysis pipeline. Notably, the computer system may take the outputs of the computer-aided detection and diagnosis and the report and may convert them to the DICOM format. Then, the computer system may provide the two new series to the user's PACS computer system.

Figure 9:
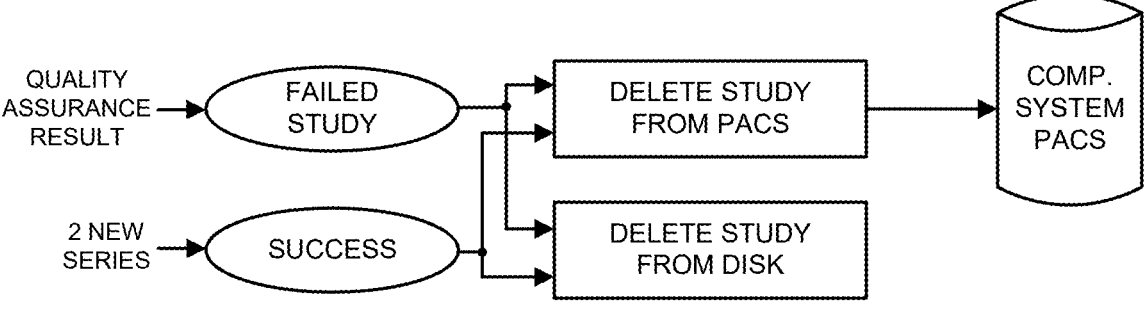
FIG. 9 is a drawing illustrating an example of study deletion in an analysis pipeline in accordance with an embodiment of the present disclosure.

In some embodiments, the computer system may optionally delete DICOM files and internal files related to or associated with a specific study. This is shown in FIG. 9, which presents a drawing illustrating an example of study deletion in an analysis pipeline. Notably, the computer system may identify a study for deletion. Note that the study to be deleted may be a study that failed quality testing or a study that has successfully reached the end of post-processing. Then, the computer system may delete internal files associated with the study identified for deletion from memory associated with the computer system.

We now further describe the pretrained predictive model. The BPRF model may be an ensemble of various base models. An ensemble model may seek the wisdom of the crowd and aggregates (e.g., average) the predictions of each base model to make a final prediction with less generalization error. BPRF may implement a chain of estimators that starts with an AdaBoost model encapsulating multiple bagging classifiers (such as Bayes estimators) that are boosted sequentially during training. Each bagging classifier may have, e.g., five parallel random forests acting on random slices of data.

Figure 10:
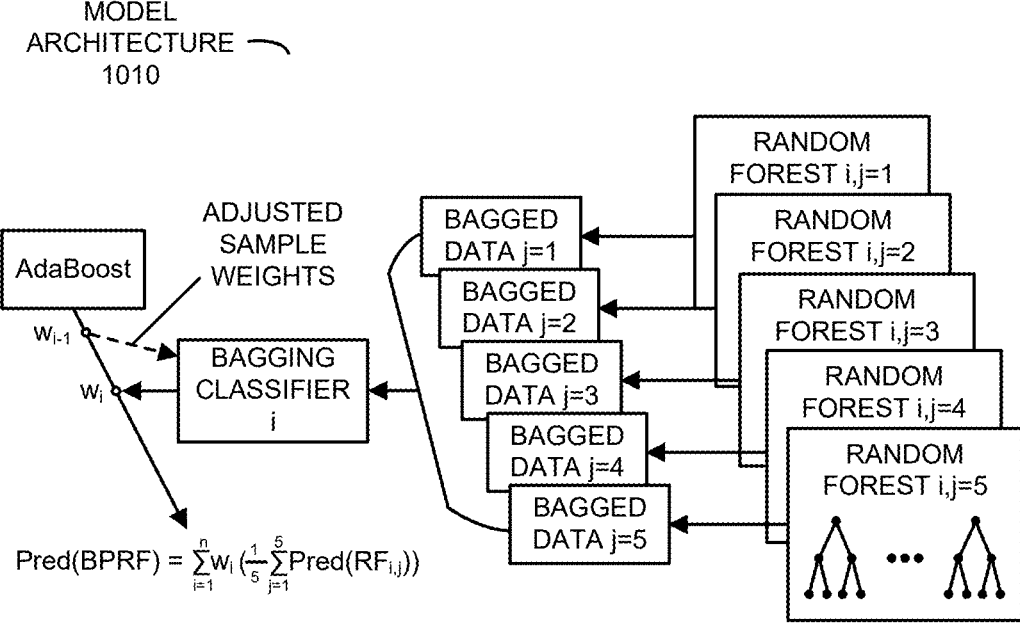
FIG. 10 is a drawing illustrating an example of a model architecture in accordance with an embodiment of the present disclosure.

Notably, the BPRF model may start by fitting a bagging estimator of, e.g., five parallel random forest classifiers on the original dataset (with a maximum depth for a given tree of 10 and with a maximum number of features used for a given decision of 6). For each boosting iteration, the bagging estimator may generate five data subsets by randomly sub-sampling 50% of both samples (voxels) and features from the original dataset and may feed each of the parallel random forests with one of them. At the end of each boosting iteration and by implementing its AdaBoost component, the BPRF model may interpret the average prediction of the bagging estimator (which may be based at least in part on the individual predictions of the five parallel random forests) and may adjust weights for incorrectly classified instances. Consequently, the subsequent bagging estimators may focus more on difficult cases and may learn how to avoid previous misclassifications. The BPRF model is shown in FIG. 10, which presents a drawing illustrating an example of a model architecture 1010.

Note that the BPRF model may be trained using a training dataset with MRI studies for 808 patients (50/50 case/control), with biological ground truth (presence or absence of cancer) determined using prostate biopsies. In some embodiments, the BPRF model may be trained using 15 boosting iterations.

Figure 11:
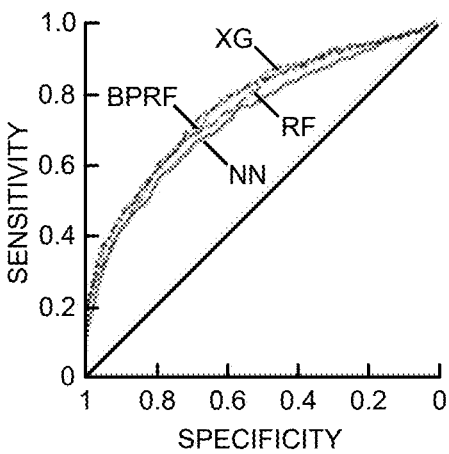
FIG. 11 is a drawing illustrating an example of receiver operator characteristics (ROCs) for different models in accordance with an embodiment of the present disclosure.
Figure 12:
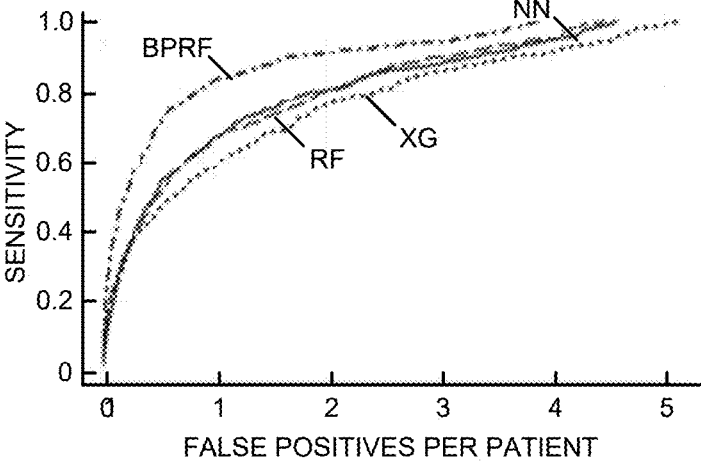
FIG. 12 is a drawing illustrating an example of free-response receiver operator characteristics (FROCs) for different models in accordance with an embodiment of the present disclosure.

Moreover, FIG. 11 presents a drawing illustrating an example of ROCs for different models evaluated at cancer-suspicious regions with biological ground truth (presence or absence of cancer) determined using prostate biopsies, and FIG. 12 presents a drawing illustrating an example of FROCs for the different models. Note that the different models in FIGS. 11 and 12 may include a BPRF model (with an AUC of 0.757 and an FROC figure of merit 0 of 0.663), a neural network or NN (with an AUC of 0.752 and an FROC figure of merit 0 of 0.537), a random forests or RF model (with an AUC of 0.754 and an FROC figure of merit 0 of 0.499) and an XGBoost or XG model (with an AUC of 0.756 and an FROC figure of merit 0 of 0.477) using a 5-fold cross validation technique.

While the preceding discussion illustrated the analysis techniques with a BPRF model, more generally the analysis techniques may use a predictive model that is pretrained or predetermined using a machine-learning technique (such as a supervised learning technique, an unsupervised learning technique and/or a neural network) and a training dataset. For example, the predictive model may include a classifier or a regression model that was trained using: random forests, a support vector machine technique, a classification and regression tree technique, logistic regression, LASSO, linear regression, a neural network technique (such as deep learning, a convolutional neural network technique, an autoencoder neural network or another type of neural network technique), a boosting technique, a bagging technique, another ensemble learning technique and/or another linear or nonlinear supervised-learning technique. In the present discussion, note that 'random forests' or random decision forests may include an ensemble learning technique for classification, regression and other tasks that operates by constructing a multitude of decision trees at training time. For classification tasks, the output of the random forest may be the class selected by most trees, while for regression tasks the mean or average prediction of the individual trees may be returned. Moreover, an ensemble learning technique may combine several decision trees classifiers to produce better predictive performance than a single decision tree classifier. In an ensemble model, a group of weak learners may be combined or aggregated to form a stronger learner, thereby increasing the accuracy of the model. Furthermore, bagging (or bootstrap aggregation) is a way to decrease the variance in a prediction by generating additional data for training from a dataset using combinations with repetitions to produce multiple subsets of the original data. Additionally, boosting is an iterative technique which adjusts the weight of an observation based on the last classification. If an observation was classified incorrectly, boosting tries to increase the weight of this observation in the subsequent model.

Figure 13:
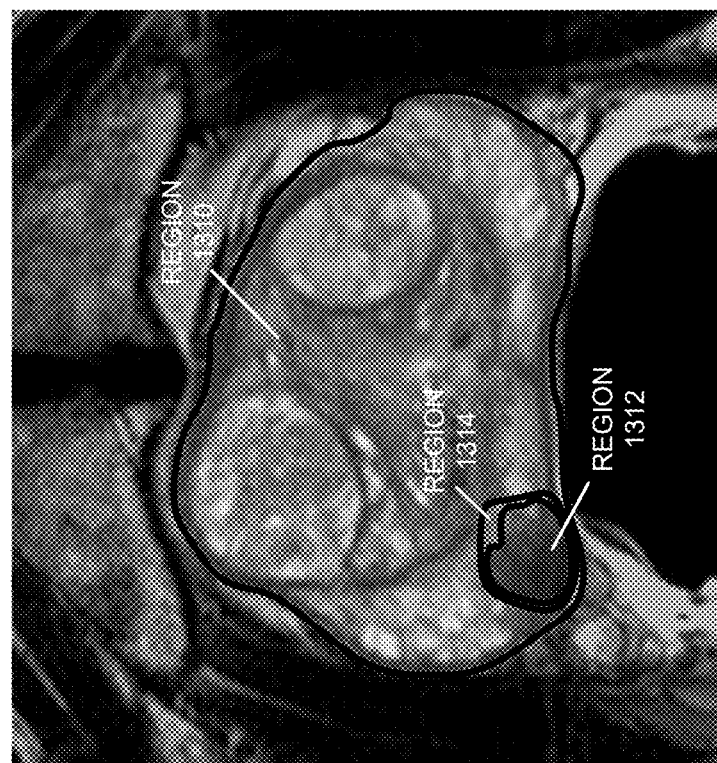
FIG. 13 is a drawing illustrating examples of an axial T2-weighted (T2 W) slice of the prostate before and after post-processing in accordance with an embodiment of the present disclosure.
Figure 13:

As discussed previously, the outputs of the analysis techniques may include: a segmentation of the whole prostate region, a segmentation of the central gland sub-region of the prostate, a color map overlay of 2D axial T2 W images that represents cancer predictions. This information is shown in FIG. 13, which presents drawings illustrating examples of an axial T2-weighted slice of the prostate before and after post-processing. In FIG. 13, region 1310 indicates normal tissue (which may be represented by the color green), region 1312 indicates a region with the highest probability index (>0.62) of cancer (which may be represented by the color red), and the remaining region (1314) may include a region with a scaled probability of cancer (which may be represented by a color spectrum, with cool colors corresponding to the lowest probability of cancer). As described further below, note that the cancer predictions provided by the analysis techniques may be represented by a metric (which is sometimes referred to as a 'ProstatID index'). Table 2 summarizes an example of a mapping from a probability index (such as the ProstatID index) to color.

TABLE 2

| Interpretation | Color | Index Value |
|---|---|---|
| Favorable | Green | ProstatID ≤0.5 |
| Borderline | Yellow | 0.5 ≤ ProstatID ≤ 0.62 |
| Unfavorable | Red | ProstatID >0.62 |

Figure 14:
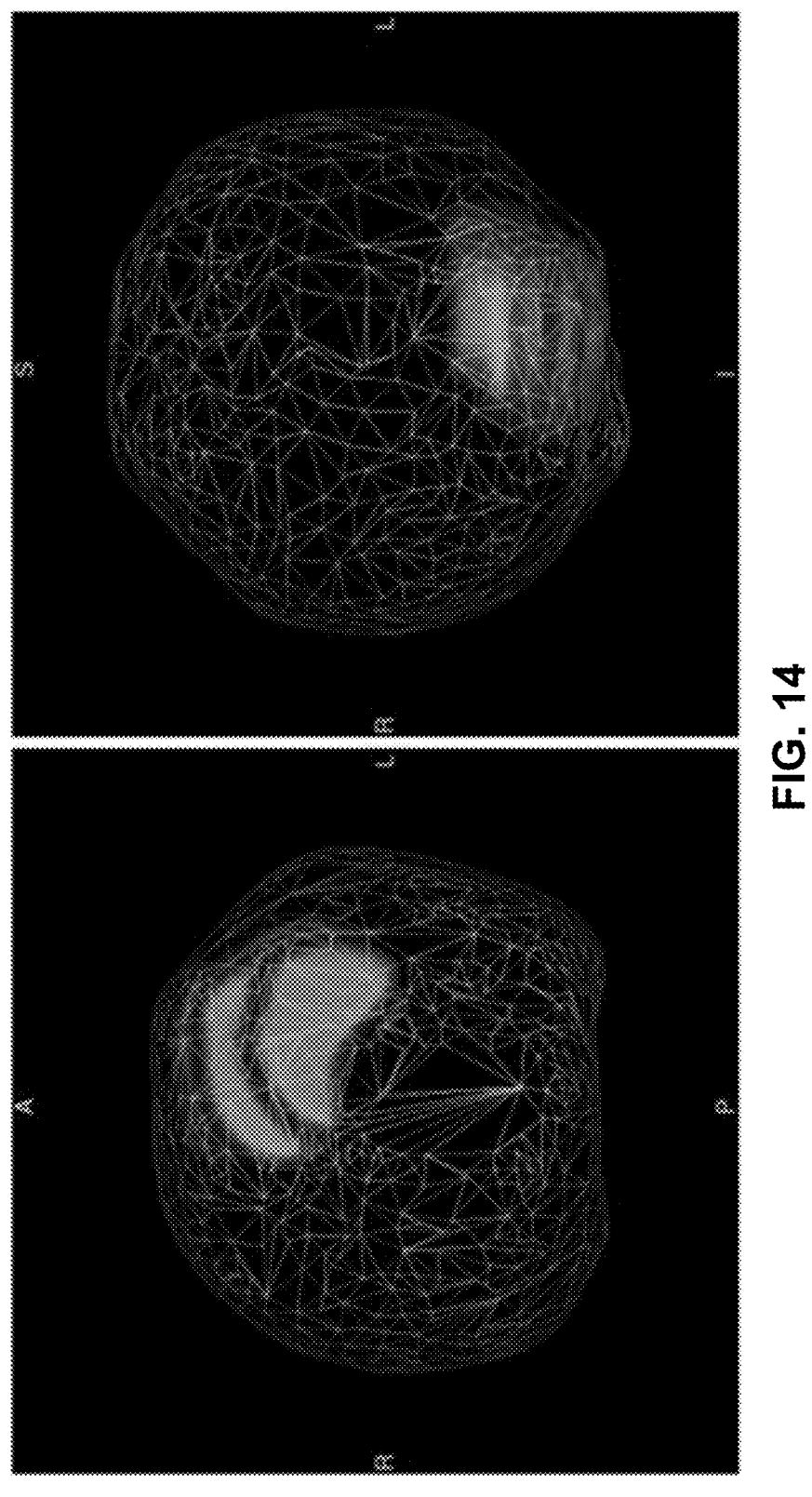
FIG. 14 is a drawing illustrating examples of a three-dimensional (3D) transparent outline of the prostate gland with a rendering of an outline of a suspected 3D solid tumor spatially located within the prostate gland in accordance with an embodiment of the present disclosure.

Furthermore, the outputs of the analysis techniques may include a three-dimensional (3D) rendition of the suspect cancerous tissue within the margins of an at least partially transparent or translucent rendition of the 3D prostate gland. This information is shown in FIG. 14, which presents a drawing illustrating examples of a 3D transparent outline of the prostate gland with a rendering of an outline of a suspected 3D solid tumor spatially located within the 3D prostate gland volume. In FIG. 14, the lesion perimeter(s) may correspond to a Prostate Imaging Reporting and Data System or PI-RADS (from the AdMeTech Foundation of Boston, Massachusetts and the European Society of Urogenital Radiology of Vienna, Austria) greater than or equal to three. The PI-RADS classification system is summarized in Table 3.

TABLE 3

| PI-RADS Score | Category | Definition |
|---|---|---|
| 5 | Very high | Clinically significant cancer is highly likely to be present |
| 4 | High | Clinically significant cancer is likely to be present |
| 3 | Intermediate | Presence of clinically significant cancer is equivocal |
| 2 | Low | Clinically significant cancer is unlikely to be present |
| 1 | Very low | Clinically significant cancer is unlikely to be present |

Figure 15:
FIG. 15 is a drawing illustrating an example of a report in accordance with an embodiment of the present disclosure.
Figure 15:
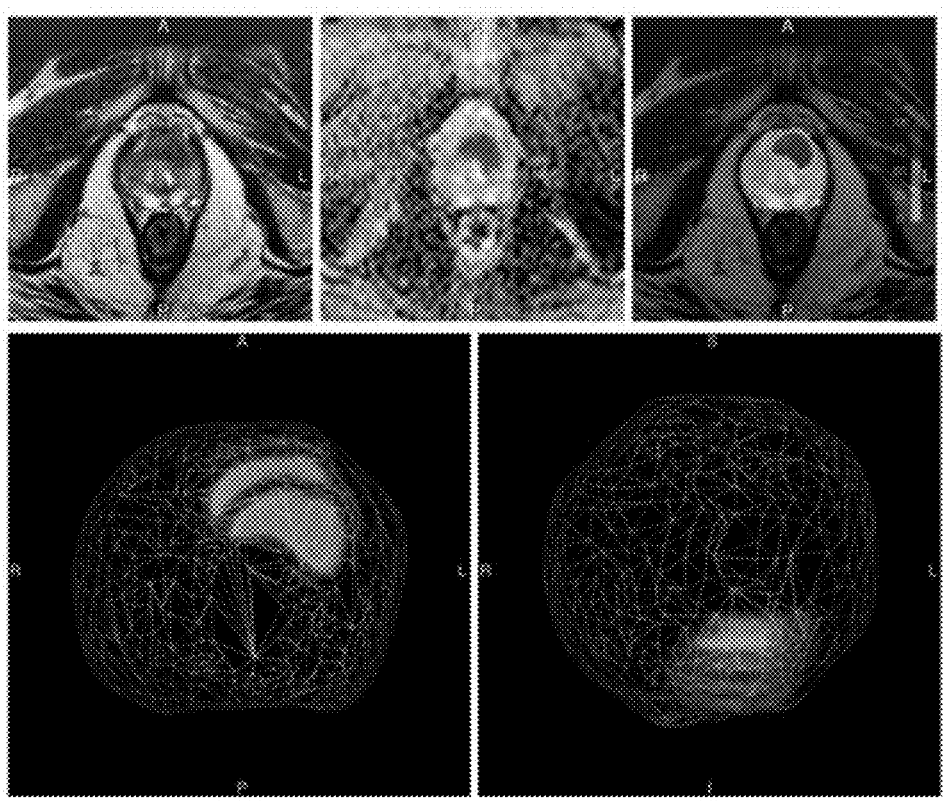

Additionally, the outputs of the analysis techniques may include a report summarizing the computer-aided detection and diagnosis results with 2D and 3D images (for predefined anatomical orientations, such as an axial view and a coronal view) indicating suspect cancerous regions, as well as the estimated volume of the prostate. This information is shown in FIG. 15, which presents a drawing illustrating an example of a report (which is sometimes referred to as a 'ProstatID report'). Note that another suspect lesion be detected, its centroid may be displayed on the 2D axial slice with the colorized probability map, as well as in the 3D rendition, in similar manner to the information shown in FIG. 15.

In the report, the ProstatID index may provide a single-value estimate of the probability or likelihood of prostate cancer. Moreover, the colorized probability index map may be correlated to the classification of cancerous tissue. In some embodiments, the outputs may be in DICOM-compliant formats. As discussed previously, this appended case study or report may be automatically returned via the same connection to a sender's or user's radiological workstation indicating a unique post-processed series number for a physician to identify the report. For example, the unique post-processed series number may append the patient study number with three digits after the study number to ensure that the user is informed that post-processing occurred, and that additional content and/or display is included.

Because the analysis techniques may be an interpretation aid for a physician, the colorized 'probability' maps may be viewed concurrently with the raw T2, DWI, and ADC images, and this information may be considered or used for: detection and localization of lesions, potentially ruling out selection of non-cancerous suspect tissues, and/or in classifying the patient case using the PI-RADS classification system.

Figure 16:
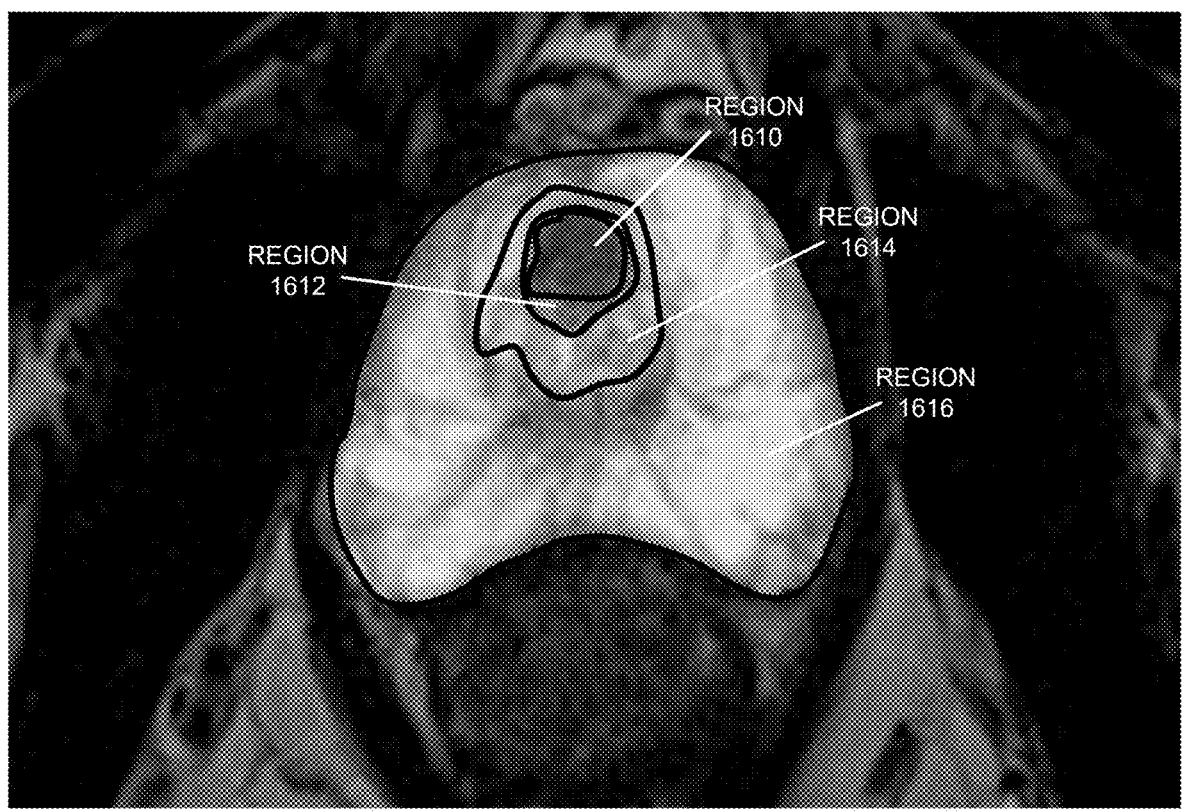
FIG. 16 is a drawing illustrating an example of color-coded regions in a T2 W image of the prostate corresponding to cancer predictions in accordance with an embodiment of the present disclosure.

FIG. 16 presents a drawing illustrating an example of color-coded regions in a T2 W image of the prostate corresponding to cancer predictions. Notably, FIG. 16 shows an example of a ProstatID color map for a patient with a Gleason 7 lesion in the transition zone of the prostate. In FIG. 16, region 1610 (which may have a color of red according to Table 4) may indicate a region highly suspicious of cancer. Moreover, region 1612 may have a color of orange/red, region 1614 may have a color of yellow, and region 1616 may have a color of green. Note that the ProstatID index and the corresponding colors in the color map (e.g., in Tables 2 and 4) may have been determined from the ROC analysis of 150 evaluation cases, which is described further below.

TABLE 4

| Color | Interpretation | Index Value | Recommended PI-RADS |
|---|---|---|---|
| Green | Favorable | ProstatID <0.500 | 1 |
| Yellow | Abnormal morphology | 0.5000 ≤ ProstatID ≤ 0.618 | 2 |
| Yellow | Suspicious | 0.500 ≤ ProstatID ≤ 0.618 | 3 |
| Orange/Red | Highly suspicious | ProstatID >0.618, lesion <1.5 cm, no extension | 4 |
| Red | Highly suspicious | ProstatID >0.618, lesion ≥1.5 cm or extension | 5 |

In some embodiments, the ProstatID index may be used to assist a physician in or to automatically assign a PI-RADS score. For example, Table 4 also provides computer-generated recommendations for PI-RADS scoring based at least in part on: the ProstatID color-coded index, morphology, the size of the primary lesion (as measured in 2D and/or 3D), and/or whether there is extraprostatic extension/invasive behavior or other complicating factors.

The analysis techniques were tested on retrospective data that represent the current standard of care and patient age demographic for prostate cancer screening. In the clinical performance assessment, the analysis techniques improved the performance of participating physicians by better correlating their PI-RADS ratings to true outcomes.

A total of 9 physicians participated in the clinical performance assessment of the analysis techniques. These physicians were blinded to the results and interpreted each case independently in two separate reads. The first read was performed without ProstatID, and second read was performed with ProstatID. Each physician (reader) described the location of suspicious lesions and assigned PI-RADS scores to each lesion in a set of 150 patients using the standard of care (without computer-aided detection and/or diagnosis). After a washout period of a minimum of 4 weeks, the readers again detected and assigned PI-RADS scores to lesions in the set of 150 patients with the aid of ProstatID (i.e., with computer-aided detection and diagnosis). Note that patient order was randomized for each reader for each read.

The 150 patient cases in the clinical assessment of ProstatID included 67 patients with clinically significant prostate cancer and 83 patients without cancer. 39 of the 83 patients without cancer had at least one suspicious lesion confirmed to be benign after biopsy, and the remaining 44 patients without cancer had normal scans. The median patient age was 67 years and ranged from 45 to 86 years. Moreover, the patients were imaged using MR scanners from different manufacturers with external magnetic-field strengths of 1.5 and 3.0 T.

Standalone diagnostic performance was assessed using the area under the curve (AUC) of the ROC curve. The value of the ProstatID index at each biopsy location was determined and compared to the true positive/true negative status of the biopsy result. Note that the ProstatID index had an AUC of 0.710 (with a 95% confidence interval of 0.643-0.778) at the biopsy locations of the 150 patient cases. (Note that the ROC and the AUC may depend on the granularity of the sampling. The aforementioned AUC is for cancer-suspicious pixels that are directly associated with biological truth points of biopsies, which is a strict evaluation that does not benefit from the performance at pixels in 'easy' regions of normal tissue. When the ROC curve is determined using all pixels or a 9 mm$^2$ grid, the AUC is greater than 0.9.) Moreover, standalone detection performance was assessed using a FROC analysis. Automatic lesion detections and their ProstatID index were compared to the locations of clinically significant cancers in the 150 patient cases. Furthermore, ProstatID achieved a sensitivity of 80% at a rate of one false positive per patient.

Clinical diagnostic performance was assessed by comparing the AUCs of the ROC curves before and after using ProstatID. The PI-RADS score assigned by the reader at the patient level was compared to the outcome of the patient. Note that the average AUC improved from 0.673 (with a 95% confidence interval of 0.584-0.761) to 0.718 (with a 95% confidence interval of 0.637-0.799). This increase is significant at the 5% level (p-value=0.0149). Clinical detection performance was assessed by comparing the weighted alternative FROC (wAFROC) performance metric before and after using ProstatID. The wAFROC metric for FROC analysis is analogous to the AUC metric for ROC analysis. The average wAFROC metric improved from 0.405 (with a 95% confidence interval of 0.266-0.544) to 0.453 (with a 95% confidence interval of 0.306-0.599). This increase is significant at the 5% level (p-value=0.024).

Finally, for the 150 patients this study, patient age and PSA level had some correlation with prostate cancer. However, the models that use these as input variables had low accuracy for predicting cancer (<61%). This highlights the need for more sophisticated techniques for cancer prediction, such as ProstatID.

While the preceding discussion illustrated the analysis techniques using certain types of medical-imaging data as inputs and providing certain information as outputs (e.g., in the report), in other embodiments the analysis techniques may use additional or different inputs and/or may provide additional or different outputs. For example, the analysis techniques may be used to determine a Gleason score or grade of a suspect cancer, which may be predicted based at least in part on the identified features using a pretrained predictive model. This capability may reduce or eliminate a need to determine a Gleason score by analyzing (via histopathology) prostate biopsy samples. Moreover, the analysis techniques may use inputs such as: a PSA level, hormone levels, genetic testing (such as protein, RNA and/or DNA information), socioeconomic data, ethnicity, information associated with an electronic medical record, etc. In some embodiments, the analysis techniques may assess medical-imaging data for an individual based at least in part on results for a population of multiple individuals.

Figure 17:
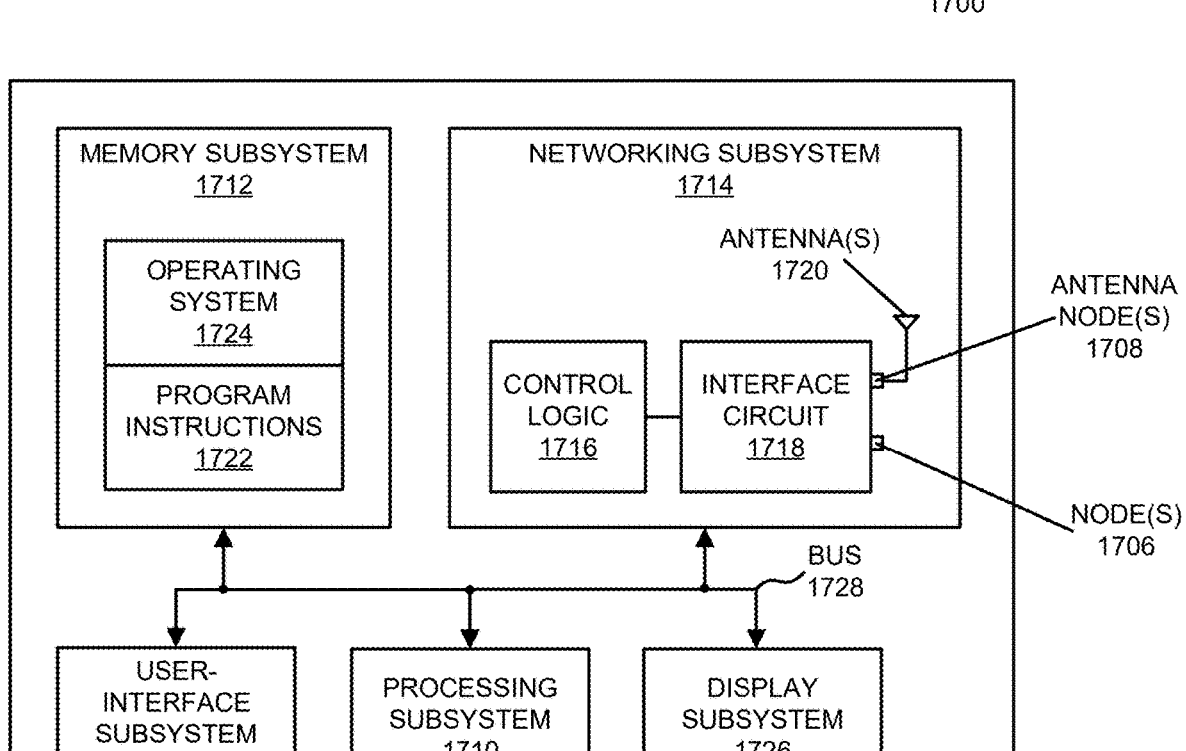
FIG. 17 is a block diagram illustrating an example of a computer in accordance with an embodiment of the present disclosure.

We now describe embodiments of a computer, which may perform at least some of the operations in the analysis techniques. FIG. 17 presents a block diagram illustrating an example of a computer 1700, e.g., in a computer system (such as computer system 100 in FIG. 1), in accordance with some embodiments. For example, computer 1700 may include: one of computers 110. This computer may include processing subsystem 1710, memory subsystem 1712, and networking subsystem 1714. Processing subsystem 1710 includes one or more devices configured to perform computational operations. For example, processing subsystem 1710 can include one or more microprocessors, ASICs, microcontrollers, programmable-logic devices, GPUs and/or one or more DSPs. Note that a given component in processing subsystem 1710 are sometimes referred to as a 'computation device'.

Memory subsystem 1712 includes one or more devices for storing data and/or instructions for processing subsystem 1710 and networking subsystem 1714. For example, memory subsystem 1712 can include dynamic random access memory (DRAM), static random access memory (SRAM), and/or other types of memory. In some embodiments, instructions for processing subsystem 1710 in memory subsystem 1712 include: program instructions or sets of instructions (such as program instructions 1722 or operating system 1724), which may be executed by processing subsystem 1710. Note that the one or more computer programs or program instructions may constitute a computer-program mechanism. Moreover, instructions in the various program instructions in memory subsystem 1712 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 1710.

In addition, memory subsystem 1712 can include mechanisms for controlling access to the memory. In some embodiments, memory subsystem 1712 includes a memory hierarchy that includes one or more caches coupled to a memory in computer 1700. In some of these embodiments, one or more of the caches is located in processing subsystem 1710.

In some embodiments, memory subsystem 1712 is coupled to one or more high-capacity mass-storage devices (not shown). For example, memory subsystem 1712 can be coupled to a magnetic or optical drive, a solid-state drive, or another type of mass-storage device. In these embodiments, memory subsystem 1712 can be used by computer 1700 as fast-access storage for often-used data, while the mass-storage device is used to store less frequently used data.

Networking subsystem 1714 includes one or more devices configured to couple to and communicate on a wired and/or wireless network (i.e., to perform network operations), including: control logic 1716, an interface circuit 1718 and one or more antennas 1720 (or antenna elements). (While FIG. 17 includes one or more antennas 1720, in some embodiments computer 1700 includes one or more nodes, such as antenna nodes 1708, e.g., a metal pad or a connector, which can be coupled to the one or more antennas 1720, or nodes 1706, which can be coupled to a wired or optical connection or link. Thus, computer 1700 may or may not include the one or more antennas 1720. Note that the one or more nodes 1706 and/or antenna nodes 1708 may constitute input(s) to and/or output(s) from computer 1700.) For example, networking subsystem 1714 can include a Bluetooth™ networking system, a cellular networking system (e.g., a 3G/4G/5G network such as UMTS, LTE, etc.), a universal serial bus (USB) networking system, a networking system based on the standards described in IEEE 802.11 (e.g., a Wi-Fi® networking system), an Ethernet networking system, and/or another networking system.

Networking subsystem 1714 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' or a 'connection' between the electronic devices does not yet exist. Therefore, computer 1700 may use the mechanisms in networking subsystem 1714 for performing simple wireless communication between electronic devices, e.g., transmitting advertising or beacon frames and/or scanning for advertising frames transmitted by other electronic devices.

Within computer 1700, processing subsystem 1710, memory subsystem 1712, and networking subsystem 1714 are coupled together using bus 1728. Bus 1728 may include an electrical, optical, and/or electro-optical connection that the subsystems can use to communicate commands and data among one another. Although only one bus 1728 is shown for clarity, different embodiments can include a different number or configuration of electrical, optical, and/or electro-optical connections among the subsystems.

In some embodiments, computer 1700 includes a display subsystem 1726 for displaying information on a display, which may include a display driver and the display, such as a liquid-crystal display, a multi-touch touchscreen, etc. Moreover, computer 1700 may include a user-interface subsystem 1730, such as: a mouse, a keyboard, a trackpad, a stylus, a voice-recognition interface, and/or another human-machine interface.

Computer 1700 can be (or can be included in) any electronic device with at least one network interface. For example, computer 1700 can be (or can be included in): a desktop computer, a laptop computer, a subnotebook/netbook, a server, a supercomputer, a tablet computer, a smartphone, a cellular telephone, a consumer-electronic device, a portable computing device, communication equipment, and/or another electronic device.

Although specific components are used to describe computer 1700, in alternative embodiments, different components and/or subsystems may be present in computer 1700. For example, computer 1700 may include one or more additional processing subsystems, memory subsystems, networking subsystems, and/or display subsystems. Additionally, one or more of the subsystems may not be present in computer 1700. Moreover, in some embodiments, computer 1700 may include one or more additional subsystems that are not shown in FIG. 17. Also, although separate subsystems are shown in FIG. 17, in some embodiments some or all of a given subsystem or component can be integrated into one or more of the other subsystems or component(s) in computer 1700. For example, in some embodiments program instructions 1722 are included in operating system 1724 and/or control logic 1716 is included in interface circuit 1718.

Moreover, the circuits and components in computer 1700 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 1714 and/or computer 1700. The integrated circuit may include hardware and/or software mechanisms that are used for transmitting signals from computer 1700 and receiving signals at computer 1700 from other electronic devices. Aside from the mechanisms herein described, radios are generally known in the art and hence are not described in detail. In general, networking subsystem 1714 and/or the integrated circuit may include one or more radios.

In some embodiments, an output of a process for designing the integrated circuit, or a portion of the integrated circuit, which includes one or more of the circuits described herein may be a computer-readable medium such as, for example, a magnetic tape or an optical or magnetic disk or solid state disk. The computer-readable medium may be encoded with data structures or other information describing circuitry that may be physically instantiated as the integrated circuit or the portion of the integrated circuit. Although various formats may be used for such encoding, these data structures are commonly written in: Caltech Intermediate Format (CIF), Calma GDS II Stream Format (GDSII), Electronic Design Interchange Format (EDIF), OpenAccess (OA), or Open Artwork System Interchange Standard (OASIS). Those of skill in the art of integrated circuit design can develop such data structures from schematics of the type detailed above and the corresponding descriptions and encode the data structures on the computer-readable medium. Those of skill in the art of integrated circuit fabrication can use such encoded data to fabricate integrated circuits that include one or more of the circuits described herein.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the analysis techniques may be implemented using program instructions 1722, operating system 1724 (such as a driver for interface circuit 1718) or in firmware in interface circuit 1718. Thus, the analysis techniques may be implemented at runtime of program instructions 1722. Alternatively or additionally, at least some of the operations in the analysis techniques may be implemented in a physical layer, such as hardware in interface circuit 1718.

In the preceding description, we refer to 'some embodiments'. Note that 'some embodiments' describes a subset of all of the possible embodiments, but does not always specify the same subset of embodiments. Moreover, note that the numerical values provided are intended as illustrations of the analysis techniques. In other embodiments, the numerical values can be modified or changed.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A computer system, comprising:
an interface circuit;
a computation device coupled to the interface circuit; and
memory, coupled to the computation device, configured to store program instructions, wherein, when executed by the computation device, the program instructions cause the computer system to perform one or more operations comprising:
receiving medical-imaging data associated with a pelvic region of an individual;
computing features associated with voxels corresponding to a prostate of the individual based at least in part on the medical-imaging data, wherein, for a given voxel, the features comprise: intensity features, texture features, and a spatial feature corresponding to a distance from a peripheral zone of the prostate to a transition zone of the prostate;
determining, on a voxel-by-voxel basis, cancer predictions for the voxels based at least in part on the computed features and a pretrained predictive model, wherein the pretrained predictive model comprises a boosted parallel random forests (BPRF) model, wherein the pretrained BPRF model comprises a boosted ensemble of bagging ensemble models, and wherein a given bagging ensemble model comprises an ensemble of random forests models; and
providing feedback based at least in part on the cancer predictions for the voxels, wherein, for the given voxel, the feedback comprises: a cancer prediction and a location.

2. The computer system of claim 1, wherein the medical-imaging data comprise magnetic-resonance-imaging studies of the individual; and
wherein the magnetic-resonance-imaging studies comprise: transverse relaxation time-weighted (T2 W) images, apparent diffusion coefficient (ADC) images, and diffusion-weighted imaging (DWI) images.

3. The computer system of claim 2, wherein the operations comprise registering a first volume corresponding to the ADC images and a second volume corresponding to the DWI images with a third volume corresponding to the T2 W images; and
wherein the registration comprises aligning the first volume and the second volume with the third volume, and correcting the second volume for distortion.

4. The computer system of claim 3, wherein the registration is based at least in part on mutual information between a give pair of volumes in the first volume, the second volume and the third volume.

5. The computer system of claim 3, wherein the registration is based at least in part on a Bayesian technique.

6. The computer system of claim 1, wherein the operations comprise segmenting the medical-imaging data to identify the voxels corresponding to the prostate.

7. The computer system of claim 6, wherein the segmenting further identifies sub-regions of the prostate.

8. The computer system of claim 1, wherein the intensity features comprise radiomics features and the texture features comprise Haralick texture features.

9. The computer system of claim 1, wherein the boosted ensemble is based at least in part on an adaptive boosting technique and the bagging ensemble is based at least in part on a Bayesian estimator technique.

10. The computer system of claim 1, wherein the boosted ensemble is computed sequentially and the bagging ensemble is computed in parallel.

11. The computer system of claim 1, wherein the feedback comprises an image indicating first regions of the prostate where the cancer predictions exceed a first threshold value.

12. The computer system of claim 11, wherein the feedback comprises the image indicating second regions of the prostate where the cancer predictions are less than the first threshold value and greater than a second threshold value.

13. The computer system of claim 1, wherein the feedback comprises an image with an at least partially transparent three-dimensional (3D) rendering of the prostate and one or more color-coded regions in the 3D rendering corresponding to cancer predictions exceeding a threshold value.

14. The computer system of claim 1, wherein, for the given voxel, the feedback indicates an aggressiveness of predicted cancer based at least in part on the cancer predictions.

15. The computer system of claim 1, wherein the feedback comprises or corresponds to a recommended therapy based at least in part on the cancer predictions.

16. A non-transitory computer-readable storage medium for use in conjunction with a computer system, the computer-readable storage medium configured to store program instructions that, when executed by the computer system, causes the computer system to perform one or more operations comprising:
receiving medical-imaging data associated with a pelvic region of an individual;
computing features associated with voxels corresponding to a prostate of the individual based at least in part on the medical-imaging data, wherein, for a given voxel, the features comprise:
intensity features, texture features, and a spatial feature corresponding to a distance from a peripheral zone of the prostate to a transition zone of the prostate;
determining, on a voxel-by-voxel basis, cancer predictions for the voxels based at least in part on the computed features and a pretrained predictive model, wherein the pretrained predictive model comprises a boosted parallel random forests (BPRF) model, wherein the pretrained BPRF model comprises a boosted ensemble of bagging ensemble models, and wherein a given bagging ensemble model comprises an ensemble of random forests models; and
providing feedback based at least in part on the cancer predictions for the voxels, wherein, for the given voxel, the feedback comprises: a cancer prediction and a location.

17. The non-transitory computer-readable storage medium of claim 16, wherein the boosted ensemble is based at least in part on an adaptive boosting technique and the bagging ensemble is based at least in part on a Bayesian estimator technique.

18. A method for providing feedback, comprising:

by a computer system:

receiving medical-imaging data associated with a pelvic region of an individual;

computing features associated with voxels corresponding to a prostate of the individual based at least in part on the medical-imaging data, wherein, for a given voxel, the features comprise: intensity features, texture features, and a spatial feature corresponding to a distance from a peripheral zone of the prostate to a transition zone of the prostate;

determining, on a voxel-by-voxel basis, cancer predictions for the voxels based at least in part on the computed features and a pretrained predictive model, wherein the pretrained predictive model comprises a boosted parallel random forests (BPRF) model, wherein the pretrained BPRF model comprises a boosted ensemble of bagging ensemble models, and wherein a given bagging ensemble model comprises an ensemble of random forests models; and providing the feedback based at least in part on the cancer predictions for the voxels, wherein, for the given voxel, the feedback comprises: a cancer prediction and a location.

19. The method of claim 18, wherein the boosted ensemble is based at least in part on an adaptive boosting technique and the bagging ensemble is based at least in part on a Bayesian estimator technique.

20. The method of claim 18, wherein the boosted ensemble is computed sequentially and the bagging ensemble is computed in parallel.

\* \* \* \* \*